(12) United States Patent
Ting

(10) Patent No.: US 12,023,195 B2
(45) Date of Patent: Jul. 2, 2024

(54) SERRATED STETHOSCOPE TUBING

(71) Applicant: MDF Instruments USA LLC, Rincon, PR (US)

(72) Inventor: Darren Talun Chiao Ting, Rincon, PR (US)

(73) Assignee: MDF Instruments USA LLC, Rincon, PR (US)

( * ) Notice: Subject to any disclaimer, the term of this patent is extended or adjusted under 35 U.S.C. 154(b) by 0 days.

(21) Appl. No.: 17/966,726

(22) Filed: Oct. 14, 2022

(65) Prior Publication Data

US 2023/0121947 A1    Apr. 20, 2023

Related U.S. Application Data

(60) Provisional application No. 63/256,522, filed on Oct. 15, 2021.

(51) Int. Cl.
*A61B 7/02*    (2006.01)
*G10K 11/16*   (2006.01)

(52) U.S. Cl.
CPC .............. *A61B 7/02* (2013.01); G10K 11/16 (2013.01)

(58) Field of Classification Search
CPC .......... A61B 7/02; G10K 11/16; G10K 11/08; G10K 11/22
USPC ....................................................... 181/131
See application file for complete search history.

(56) References Cited

U.S. PATENT DOCUMENTS

| | | | | |
|---|---|---|---|---|
| 2,799,270 A | * | 7/1957 | Rodbard | A61B 7/02 600/491 |
| 5,883,340 A | * | 3/1999 | Shieh | A61B 7/02 181/131 |
| 5,952,618 A | * | 9/1999 | Deslauriers | A61B 7/026 181/131 |
| 8,939,251 B2 | | 1/2015 | Ting | |
| D724,206 S | | 3/2015 | Ting | |
| D724,728 S | | 3/2015 | Ting | |
| 9,486,180 B2 | | 11/2016 | Ting | |
| D926,313 S | | 7/2021 | Ting et al. | |
| 11,666,302 B2 | | 6/2023 | Ting | |
| 2004/0226771 A1 | * | 11/2004 | Werblud | A61B 7/02 181/131 |
| 2014/0005574 A1 | | 1/2014 | Ting | |
| 2015/0129350 A1 | | 5/2015 | Ting | |
| 2021/0038183 A1 | | 2/2021 | Ting | |

FOREIGN PATENT DOCUMENTS

DE    2106249 A1 *    6/1977

OTHER PUBLICATIONS

Machine Translation of DE 2106249 A1. Inventor: SPEIDEL. (Year: 1977).*

* cited by examiner

*Primary Examiner* — Dedei K Hammond
*Assistant Examiner* — Jennifer B. Olson
(74) *Attorney, Agent, or Firm* — The Law Office of Patrick F. O'Reilly III, LLC

(57) ABSTRACT

A serrated stethoscope tube is disclosed herein. The serrated stethoscope tube includes a tubular body portion, the tubular body portion having an exterior surface and an interior surface, the interior surface being oppositely disposed relative to the exterior surface, and the interior surface of the tubular body portion having a plurality of channels formed therein for reducing sound wave refraction and/or reverberation.

8 Claims, 3 Drawing Sheets

Z-Z
10:1

SERRATED STETHOSCOPE TUBING

CROSS-REFERENCE TO RELATED APPLICATIONS

This patent application claims priority to, and incorporates by reference in its entirety, U.S. Provisional Patent Application No. 63/256,522, entitled "Serrated Stethoscope Tubing", filed on Oct. 15, 2021.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to serrated stethoscope tubing. More particularly, the invention relates to serrated stethoscope tubing having a plurality of channels formed in an interior surface thereof for reducing sound wave refraction and/or reverberation.

2. Background

It is known in the art that a medical practitioner employs various devices during the course of examination of a patient. One such instrument is a stethoscope that is used by physicians, nurses, and paramedics in the early stage of any general examination and/or proper vital sign examination of a patient.

A stethoscope is an acoustic medical device for auscultation, or listening to the internal sounds of a body. It is often used to listen to heart sounds. It is also used to listen to intestines and blood flow in arteries and veins. Acoustic stethoscopes operate on the transmission of sounds from the chestpiece, via air-filled hollow tubes, to a binaural (headset) that a practitioner uses to listen to the acoustic sounds of a patient. The chestpiece usually consists of a diaphragm and a housing that supports the diaphragm within the chestpiece body. When the diaphragm is placed on the patient, body sounds vibrate the diaphragm, creating acoustic pressure waves which travel up the tubing to the binaural and the listener's ears.

The proper operation of a stethoscope is essential, since a practitioner, nurse or a doctor, uses a stethoscope to listen to the sounds of a patient's body to determine normal functioning and abnormalities.

The acoustic tube of a conventional stethoscope has an interior surface that is generally smooth. Consequently, sound waves, which emanate from the stethoscope chestpiece, tend to refract and reverberate as the sound waves are transported within the interior passageway of the acoustic tube up to the headset of the stethoscope. This refraction and reverberation makes it more difficult for a user of the stethoscope to hear clear and precise sound waves that are generated from the patient's body.

Therefore, what is needed is a serrated stethoscope tube that has a plurality of channels formed in an interior surface thereof for reducing sound wave refraction and/or reverberation. In addition, a serrated stethoscope tube is needed that is able to clearly and precisely transmit sound waves generated by a patient to the ears of a medical professional.

BRIEF SUMMARY OF EMBODIMENTS OF THE INVENTION

Accordingly, the present invention is directed to a serrated stethoscope tube that substantially obviates one or more problems resulting from the limitations and deficiencies of the related art.

In accordance with one or more embodiments of the present invention, there is provided a serrated stethoscope tube that includes a tubular body portion, the tubular body portion having an exterior surface and an interior surface, the interior surface being oppositely disposed relative to the exterior surface, and the interior surface of the tubular body portion having a plurality of channels formed therein for reducing sound wave refraction and/or reverberation.

In a further embodiment of the present invention, the plurality of channels formed in the tubular body portion extend in a longitudinal direction of the serrated stethoscope tube.

In yet a further embodiment, at least some of the plurality of channels formed in the tubular body portion are separated from one another by a protruding element.

In still a further embodiment, the plurality of channels formed in the tubular body portion are circumferentially spaced apart from one another about a periphery of the interior surface of the tubular body portion.

In yet a further embodiment, at least some of the plurality of channels have a generally flat bottom.

In still a further embodiment, the tubular body portion has a wall thickness of at least 2.0 millimeters.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
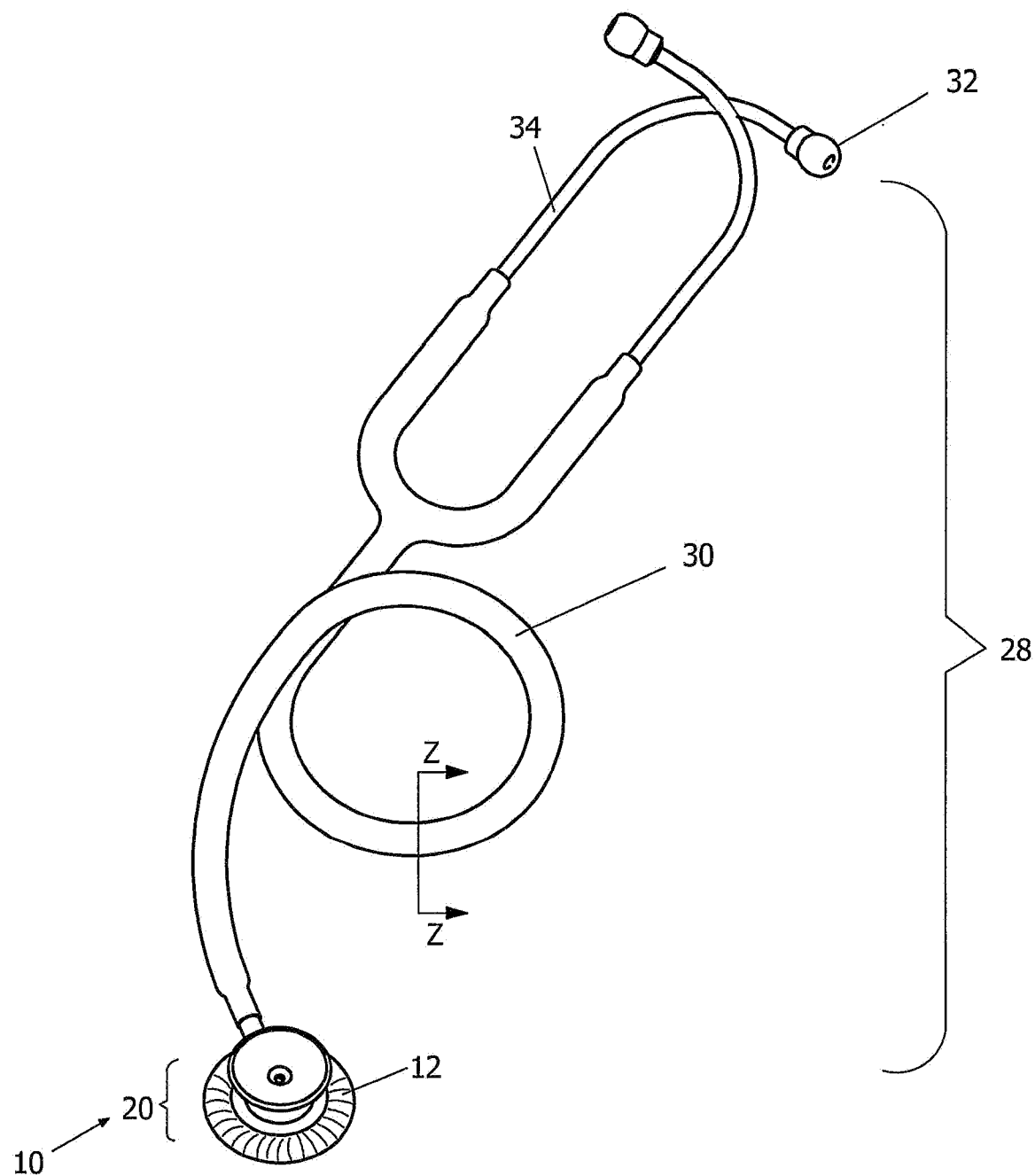
FIG. 1 is a perspective view of a stethoscope with a chestpiece having a serrated acoustic tube, according to an illustrative embodiment of the invention.

An illustrative embodiment of a stethoscope having a serrated acoustic tube is seen generally at 10 in FIG. 1. As shown in FIG. 1, the stethoscope 10 generally comprises a chestpiece assembly 20 and a binaural assembly 28 that includes two earpieces 32. Also, as illustrated in FIG. 1, the binaural assembly 28 of the stethoscope 10 includes a serrated acoustic tube 30 that is acoustically coupled to a headset with two (2) ear tubes 34. Each of the ear tubes 34 is provided with a respective earpiece 32 disposed on a proximal end thereof. In addition, as shown in FIG. 1, the chestpiece 20 of the stethoscope 10 is provided with a diaphragm and ring 12 fitted thereon, which may comprise a one-piece diaphragm and ring.

Now, with reference again to FIG. 1, the illustrative embodiment of the chestpiece 20 of the stethoscope 10 will be described. As shown in this figure, it can be seen that the stethoscope chestpiece 20 generally includes a chestpiece body portion having a first end and a second end, a frusto-conical bell portion at the first end of the chestpiece body portion, and a diaphragm and ring 12 attached to the second end of the chestpiece body portion.

Figure 2:
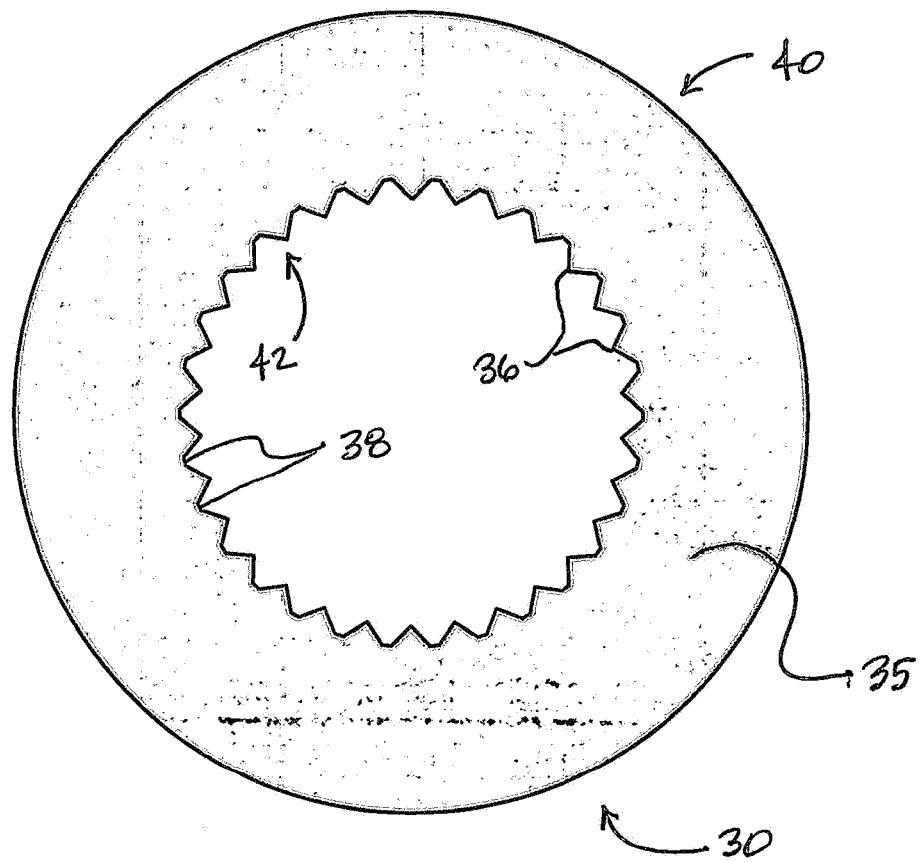
FIG. 2 is an enlarged cross-sectional view of the serrated acoustic tube of the stethoscope of FIG. 1, which is cut along the cutting-plane line Z-Z extending transversely through the serrated acoustic tube in FIG. 1.
Figure 3:
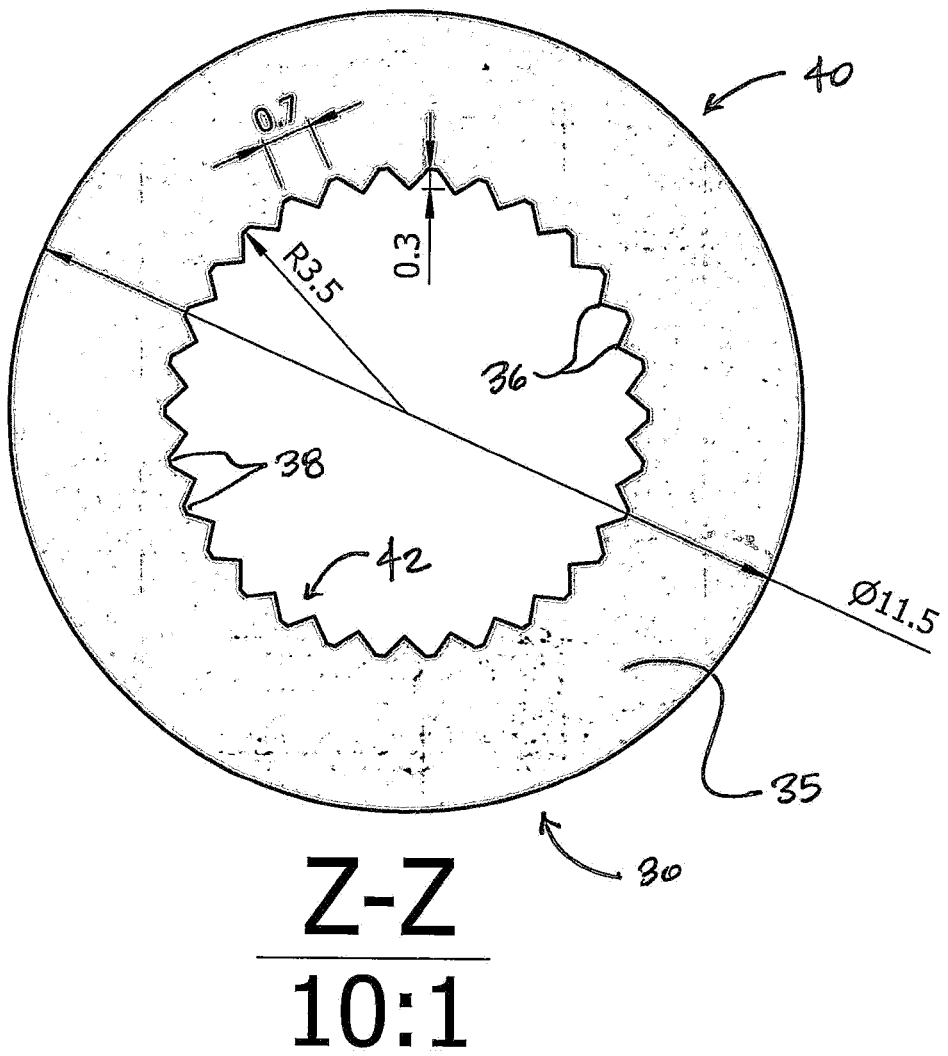
FIG. 3 is another enlarged cross-sectional view of the serrated acoustic tube of the stethoscope of FIG. 1 with exemplary dimensional information, which is cut along the cutting-plane line Z-Z extending transversely through the serrated acoustic tube in FIG. 1.

Turning again to FIG. 1, the illustrative embodiment of the binaural assembly 28 of the stethoscope 10 will be described. In the illustrative embodiment, the binaural assembly 28 generally includes first and second ear tubes 34, and a serrated acoustic tube 30 connected to the first and second ear tubes 34. With combined reference to the cross-sectional views of FIGS. 2 and 3, it can be seen that the serrated acoustic tube 30 comprises a tubular body portion 35, the tubular body portion 35 having an exterior surface 40 and an interior surface 42, the interior surface 42 being oppositely disposed relative to the exterior surface 40, and the interior surface 42 of the tubular body portion 35 having a plurality of channels 38 formed therein for reducing sound wave refraction and/or reverberation. In the illustrative embodiment, the plurality of channels 38 formed in the tubular body portion 35 extend in a longitudinal direction of the serrated stethoscope tube 30.

Referring again to FIGS. 2 and 3, in the illustrative embodiment, each of the plurality of channels 38 formed in the tubular body portion 35 of the serrated acoustic tube 30 is separated from one another by a protruding element 36 (e.g., a protruding triangular peak 36). Also, in the illustrative embodiment, the plurality of channels 38 formed in the tubular body portion 35 are circumferentially spaced apart from one another about a periphery of the interior surface 42 of the tubular body portion 35. In addition, as shown in the illustrative embodiment of FIGS. 2 and 3, each of the plurality of channels 38 in the tubular body portion 35 has a generally flat bottom.

In the illustrative embodiment, each of the plurality of channels 38 formed in the tubular body portion 35 of the serrated acoustic tube 30 may have a channel depth between approximately 0.2 millimeters and approximately 0.5 millimeters (or between 0.2 millimeters and 0.5 millimeters). More particularly, with reference to the illustrative embodiment of FIG. 3, each of the plurality of channels 38 formed in the tubular body portion 35 of the serrated acoustic tube 30 may have a channel depth of approximately 0.3 millimeters. Also, in the illustrative embodiment, the center-to-center spacing between the channels 38 formed in the tubular body portion 35 of the serrated acoustic tube 30 may be between approximately 0.5 millimeters and approximately 1.0 millimeters (or between 0.5 millimeters and 1.0 millimeters). More particularly, with reference to the illustrative embodiment of FIG. 3, the center-to-center spacing between the channels 38 formed in the tubular body portion 35 of the serrated acoustic tube 30 may be approximately 0.7 millimeters.

In the illustrative embodiment, the serrated acoustic tube 30 may have an outer diameter of between approximately 10.0 millimeters and approximately 12.0 millimeters (or between 10.0 millimeters and 12.0 millimeters). More particularly, with reference to the illustrative embodiment of FIG. 3, the serrated acoustic tube 30 may have an outer diameter of approximately 11.5 millimeters. Also, in the illustrative embodiment, the serrated acoustic tube 30 may have an inner radius of between approximately 3.0 millimeters and approximately 5.0 millimeters (or between 3.0 millimeters and 5.0 millimeters). More particularly, with reference to the illustrative embodiment of FIG. 3, the serrated acoustic tube 30 may have an inner radius of approximately 3.5 millimeters.

In the illustrative embodiment, the tubular body portion 35 of the serrated acoustic tube 30 may have a wall thickness of at least 2.0 millimeters. More particularly, with reference to the illustrative embodiment of FIG. 3, the serrated acoustic tube 30 may have a wall thickness of approximately 2.25 millimeters.

In the illustrative embodiment, the tubular body portion 35 of the serrated acoustic tube 30 may have between twenty (20) and forty (40) channels 38 formed into the interior surface 42 thereof. More particularly, in the illustrative embodiment, the tubular body portion 35 of the serrated acoustic tube 30 may have between thirty (30) and thirty-five (35) channels 38 formed into the interior surface 42 thereof.

It is readily apparent that the aforedescribed serrated stethoscope tube 30 offers numerous advantages. First of all, the serrated stethoscope tube 30 has a plurality of channels 38 formed in an interior surface 42 thereof for reducing sound wave refraction and/or reverberation. Secondly, the serrated stethoscope tube 30 is able to clearly and precisely transmit sound waves generated by a patient to the ears of a medical professional. The serrated stethoscope tube 30 described above reduces the echoes associated with conventional stethoscope tubes that have generally smooth interior surfaces. The serrated stethoscope tube 30 helps to eliminate reverberation so that the S1, S2, S3, and S4 heart sounds and the subtle gaps therebetween are not filled with delayed reflected sound, thereby making it easier for a medical professional to hear these sounds when examining a patient with his or her stethoscope.

Any of the features or attributes of the above-described embodiments and variations can be used in combination with any of the other features and attributes of the above described embodiments and variations as desired. All numerical ranges described above with respect to the illustrative embodiments are inclusive of all numerical values within the range as well as the two endpoints of the range.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A serrated stethoscope tube, comprising:
a tubular body portion, the tubular body portion having an exterior surface and an interior surface, the exterior surface being a continuous circular surface extending in a longitudinal direction of the serrated stethoscope tube, the interior surface being oppositely disposed relative to the exterior surface, and the interior surface of the tubular body portion having a plurality of channels formed therein for reducing sound wave refraction and/or reverberation, each of the plurality of channels having a bottom wall extending in the longitudinal direction of the serrated stethoscope tube.

2. The serrated stethoscope tube according to claim 1, wherein at least some of the plurality of channels formed in the tubular body portion have a continuous V-shaped cross-section extending in the longitudinal direction of the serrated stethoscope tube.

3. The serrated stethoscope tube according to claim 1, wherein at least some of the plurality of channels formed in the tubular body portion are separated from one another by a protruding element defining a peak.

4. The serrated stethoscope tube according to claim 1, wherein the plurality of channels formed in the tubular body portion are circumferentially spaced apart from one another about a periphery of the interior surface of the tubular body portion.

5. The serrated stethoscope tube according to claim 1, wherein the bottom wall of at least some of the plurality of channels comprise a generally flat bottom wall.

6. The serrated stethoscope tube according to claim 1, wherein the tubular body portion has a wall thickness of at least 2.0 millimeters.

7. The serrated stethoscope tube according to claim 3, wherein the peak of the protruding element extends in the longitudinal direction of the serrated stethoscope tube.

8. The serrated stethoscope tube according to claim 3, wherein the tubular body portion has a first wall thickness measured from the peak of the protruding element to the exterior surface and a second wall thickness measured from the bottom wall of the protruding element to the exterior surface, the first wall thickness being greater than the second wall thickness.

* * * * *